(12) United States Patent
Zhou et al.

(10) Patent No.: US 10,834,308 B2
(45) Date of Patent: Nov. 10, 2020

(54) REAL TIME CONTROLLER SWITCHING

(71) Applicant: Illumina, Inc., San Diego, CA (US)

(72) Inventors: Chunhong (Allen) Zhou, San Diego, CA (US); John Bailey, San Diego, CA (US); Dustin Blair, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 12 days.

(21) Appl. No.: 16/245,128

(22) Filed: Jan. 10, 2019

(65) Prior Publication Data

US 2019/0222743 A1 Jul. 18, 2019

Related U.S. Application Data

(60) Provisional application No. 62/617,062, filed on Jan. 12, 2018.

(30) Foreign Application Priority Data

Mar. 20, 2018 (NL) ...................................... 2020618

(51) Int. Cl.
*H04N 5/232* (2006.01)
*G02B 26/10* (2006.01)
(Continued)

(52) U.S. Cl.
CPC ....... *H04N 5/23212* (2013.01); *G02B 21/002* (2013.01); *G02B 21/0036* (2013.01);
(Continued)

(58) Field of Classification Search
CPC ........... H04N 5/23212; H04N 5/23216; H04N 5/23245; H04N 5/2356; G02B 21/26;
(Continued)

(56) References Cited

U.S. PATENT DOCUMENTS

| 5,475,291 | A | 12/1995 | Yoshida et al. |
| 6,611,119 | B2 | 8/2003 | Fu |

(Continued)

FOREIGN PATENT DOCUMENTS

| EP | 0790543 B1 | 5/2000 |
| EP | 3151052 | 4/2017 |

(Continued)

*Primary Examiner* — Abdelaaziz Tissire
(74) *Attorney, Agent, or Firm* — Illumina, Inc.

(57) ABSTRACT

An imaging system may include a sample stage having a surface to support a sample to be scanned by the imaging system; an optical stage having an objective lens, the optical stage being positionable relative to the sample stage; an actuator physically coupled to at least one of the sample stage and the optical stage to move the sample stage relative to the optical stage; a servo circuit to control the actuator; a first set of control parameters to control the servo circuit; a second set of control parameters to control the servo circuit; and a servo control circuit to apply the first set of control parameters to the servo circuit when the imaging system is operating in a first mode of operation and to apply the second set of control parameters to the servo circuit when the imaging system is operating in a second mode of operation.

33 Claims, 11 Drawing Sheets

(51) Int. Cl.
*G02B 21/00* (2006.01)
*G02B 21/36* (2006.01)
*G02B 21/26* (2006.01)

(52) U.S. Cl.
CPC .............. *G02B 21/26* (2013.01); *G02B 21/36* (2013.01); *G02B 26/10* (2013.01); *H04N 5/23216* (2013.01); *H04N 5/23245* (2013.01)

(58) Field of Classification Search
CPC .. G02B 21/0036; G02B 21/36; G02B 21/002; G02B 26/10; G02B 21/241; G02B 21/365; G02B 7/285; G02B 7/32; G02B 7/09; G02B 7/102; G02B 7/28–40; G01N 21/6456; G01N 2021/0162; G01N 21/01; C12Q 1/68; G05B 11/42; G03B 13/36; G06T 2207/10056–10061

See application file for complete search history.

(56) References Cited

U.S. PATENT DOCUMENTS

| | | |
|---|---|---|
| 8,410,414 B2 | 4/2013 | Wu et al. |
| 2004/0029213 A1* | 2/2004 | Callahan ............ G01N 15/1475 435/40.5 |
| 2007/0194225 A1 | 8/2007 | Zorn |
| 2010/0111768 A1* | 5/2010 | Banerjee ............... C12Q 1/6869 422/82.08 |
| 2010/0157086 A1* | 6/2010 | Segale ............... G01N 21/6458 348/222.1 |
| 2010/0193704 A1* | 8/2010 | Pratt .................... G01J 3/4406 250/459.1 |
| 2012/0002274 A1 | 1/2012 | Knoblich et al. |
| 2015/0130920 A1* | 5/2015 | Zou ...................... G02B 21/006 348/79 |
| 2016/0344911 A1* | 11/2016 | Wang ................... H04N 5/2256 |
| 2018/0188514 A1* | 7/2018 | Arianpour ........... G02B 21/002 |
| 2018/0262670 A1* | 9/2018 | Condello .............. G02B 21/06 |

FOREIGN PATENT DOCUMENTS

| | | |
|---|---|---|
| JP | 3368934 | 1/2003 |
| RU | 2540453 | 2/2015 |
| WO | 2012/056920 | 5/2012 |

* cited by examiner

REAL TIME CONTROLLER SWITCHING

CROSS-REFERENCE TO RELATED APPLICATIONS

The present application claims priority to U.S. Provisional Patent Application No. 62/617,062 filed on Jan. 12, 2018 and entitled "Real Time Controller Switching," and Dutch Patent Application No. N2020618 filed on Mar. 20, 2018 and entitled "Real Time Controller Switching." The entire contents of each of the aforementioned applications are incorporated herein by reference.

BACKGROUND

Numerous advances in the field of biology have benefited from improved imaging systems and techniques, such as, for example, those used in optical microscopes and image scanning systems. Achieving accurate focus during imaging using these imaging systems can be important for successful imaging operations. Also important is the ability to perform high-speed scanning to achieve high imaging quality at high throughputs.

Focusing operations for both focus model generation and image scanning often depend on movement of a sample stage relative to an optical stage so that the sample is positioned in the focal plane of the objective lens or other optics in the optical stage. Typically, an actuator, such as a motor, coil, or other drive system is used to move the optical stage or the sample stage, or both, to achieve proper focus. A servo system may be implemented to allow precise control of the actuator.

FIG. 1 illustrates an example of a servo system that can be used for actuator control. In this example, a drive signal 3 is supplied to the servo system indicating a desired position of the actuator. Feedback 5 from the controlled process 20 is subtracted from the drive signal 3 to produce an error signal 9 indicating the error in actual position from the desired position. The server controller 10 adjusts the signal 7 supplied to control the actuator based on the amount of error detected. In this example, the servo system is a proportional-integral-derivative (PID) controller system including proportional 12, integral 13 and derivative 14 controls.

SUMMARY

Systems and methods disclosed herein may be implemented to optimize a servo control system implemented to control an actuator used for focusing operations in an imaging system. The optimization techniques can be implemented such that, during operation of the imaging system, the current mode of operation of the imaging system can be determined. For example, the mode of operation can include a focus model generation mode and an imaging or sequencing mode. In some applications, different sets of operating parameters for the servo control system may be used to optimize the servo control system for the different modes of operation. Accordingly, example implementations can be configured to determine the set of operating parameters that will optimize the servo control system for the determined mode of operation, and apply this set of operating parameters to the servo system. In various applications, this can be done in real time while the imaging system is operating and switching between modes. Where the mode of operation changes, a new set of operating parameters to optimize the servo control system for the new mode of operation can be selected and applied. Again, these changes can be made in real time, while the image system is operational.

Some applications of the technology described herein may comprise an imaging system, including a sample stage including a surface to support a sample to be scanned by the imaging system; an optical stage having an objective lens, the optical stage being positionable relative to the sample stage; an actuator physically coupled to at least one of the sample stage and the optical stage to move the sample stage relative to the optical stage; a servo circuit to control the actuator; a first set of control parameters to control the servo circuit; a second set of control parameters to control the servo circuit; and a servo control circuit to apply the first set of control parameters to the servo circuit when the imaging system may be operating in a first mode of operation and to apply the second set of control parameters to the servo circuit when the imaging system may be operating in a second mode of operation. In some applications, imaging system may be a sequencer and the first mode of operation may be a focus model generation mode, and the second mode of operation may be a sequencing mode. The control parameters may include servo loop gains and filter values.

The servo control circuit may also include a mode detection circuit to detect the mode of operation of the imaging system and a parameter selection circuit to apply the set of control parameters corresponding to the detected mode of operation.

The servo control circuit may be further implemented to detect the mode of operation of the imaging system and select the set of control parameters to apply for the detected mode of operation. The servo control circuit may apply the first or second set of control parameters that are identified as being the set of control parameters for the detected mode of operation.

A least one of the first and second sets of control parameters may be optimized to account for structural characteristics of the imaging system. Optimizing at least one of the first and second sets of control parameters may include operating the imaging system, scanning through a range of values of a control parameter of a set of the first and second sets of control parameters, measuring stability of the servo circuit during the scanning and selecting a value of the control parameter. Optimizing at least one of the first and second sets of control parameters may include operating the imaging system, scanning through a range of values of a plurality of control parameters of a set of the first and second sets of control parameters, measuring stability of the servo circuit during the scanning and identifying optimal settings for the plurality of control parameters.

The imaging system may further include focus tracking circuitry electrically coupled to the optical stage; and the servo control circuit may be configured to enable feedback from the focus tracking circuitry to the servo circuit when the imaging system is operating in a scanning mode of operation and to disable feedback from the focus tracking circuitry to the servo circuit when the imaging system is operating in focus model generation mode of operation.

The actuator may be physically coupled to the sample stage to move the sample stage to adjust a distance between the sample stage and the optical stage. Alternatively, the actuator may be physically coupled to the optical stage to move the optical stage to adjust a distance between the sample stage and the optical stage. In another example, actuators may be coupled to the sample stage and the optical stage to adjust the distance between the sample stage and the optical stage.

As a further example a method of servo control for an imaging system may include: during operation of the imaging system, a mode detection circuit determining that the imaging system may be operating in a first mode of operation; a servo control circuit determining a first set of control parameters selected for the first mode of operation; the servo control circuit applying the determined first set of control parameters to a servo circuit of the imaging system, wherein the servo circuit controls operation of an actuator physically coupled to at least one of a sample stage and an optical stage of the imaging system to move the sample stage relative to the optical stage; and upon the mode detection circuit determining during operation of the imaging system that the imaging system has switched to operating in a second mode of operation, the servo control circuit determining a second set of control parameters selected for the second mode of operation and applying the determined second set of control parameters to a servo circuit. The method may further include the servo control circuit detecting the mode of operation of the imaging system and selecting the set of control parameters to apply for the detected mode of operation.

Example methods may further include the servo control circuit detecting the mode of operation of the imaging system and selecting the set of control parameters to apply for the detected mode of operation. The servo control circuit may apply the first or second set of control parameters that are identified as being the set of control parameters for the detected mode of operation.

Some methods may further include optimizing at least one of the first and second sets of control parameters to account for structural characteristics of the imaging system. Optimizing at least one of the first and second sets of control parameters may include operating the imaging system, scanning through a range of values of a control parameter of a set of the first and second sets of control parameters, measuring stability of the servo circuit during the scanning and selecting a value of the control parameter. Optimizing at least one of the first and second sets of control parameters may include operating the imaging system, scanning through a range of values of a plurality of control parameters of a set of the first and second sets of control parameters, measuring stability of the servo circuit during the scanning and identifying optimal settings for the plurality of control parameters.

In some applications the imaging system may be a sequencer and the first mode of operation may be a focus model generation mode, and the second mode of operation may be a sequencing mode. The servo control circuit may further enable feedback from focus tracking circuitry to the servo circuit when the imaging system is operating in a scanning mode of operation and to disable feedback from the focus tracking circuitry to the servo circuit when the imaging system is operating in focus model generation mode of operation.

In yet another example, an imaging system, may include; a sample stage comprising a surface to support a sample to be scanned by the imaging system; an optical stage having an objective lens, the optical stage being positionable relative to the sample stage; focus tracking circuitry coupled to the optical stage; an actuator physically coupled to at least one of the sample stage and the optical stage to move the sample stage relative to the optical stage based on information from the focus tracking circuitry; a servo circuit to control the actuator; and a servo control circuit to enable feedback from the focus tracking circuitry to the servo circuit when the imaging system is operating in a scanning mode of operation and to disable feedback from the focus tracking circuitry to the servo circuit when the imaging system is operating in focus model generation mode of operation.

In an imaging system, a method of servo control, may include: during operation of the imaging system, a mode detection circuit determining whether the imaging system is operating in a scanning mode of operation or a focus model generation mode of operation; a servo circuit controlling movement of an optical stage relative to a sample stage in the imaging system; and a servo control circuit enabling feedback from focus tracking circuitry to the servo circuit when the imaging system is operating in a scanning mode of operation and disabling feedback from the focus tracking circuitry to the servo circuit when the imaging system is operating in focus model generation mode of operation.

Other features and aspects of the disclosed technology will become apparent from the following detailed description, taken in conjunction with the accompanying drawings, which illustrate, by way of example, the features in accordance with implementations of the disclosed technology. The summary is not intended to limit the scope of any inventions described herein, which are defined by the claims and equivalents.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

The technology disclosed herein, in accordance with one or more examples, is described in detail with reference to the following figures. These figures are provided to facilitate the reader's understanding of the disclosed technology, and are not intended to be exhaustive or to limit the disclosure to the precise forms disclosed. Indeed, the drawings in the figures are provided for purposes of illustration only, and merely depict typical or example examples of the disclosed technology. Furthermore, it should be noted that for clarity and ease of illustration, the elements in the figures have not necessarily been drawn to scale.

Figure 1:
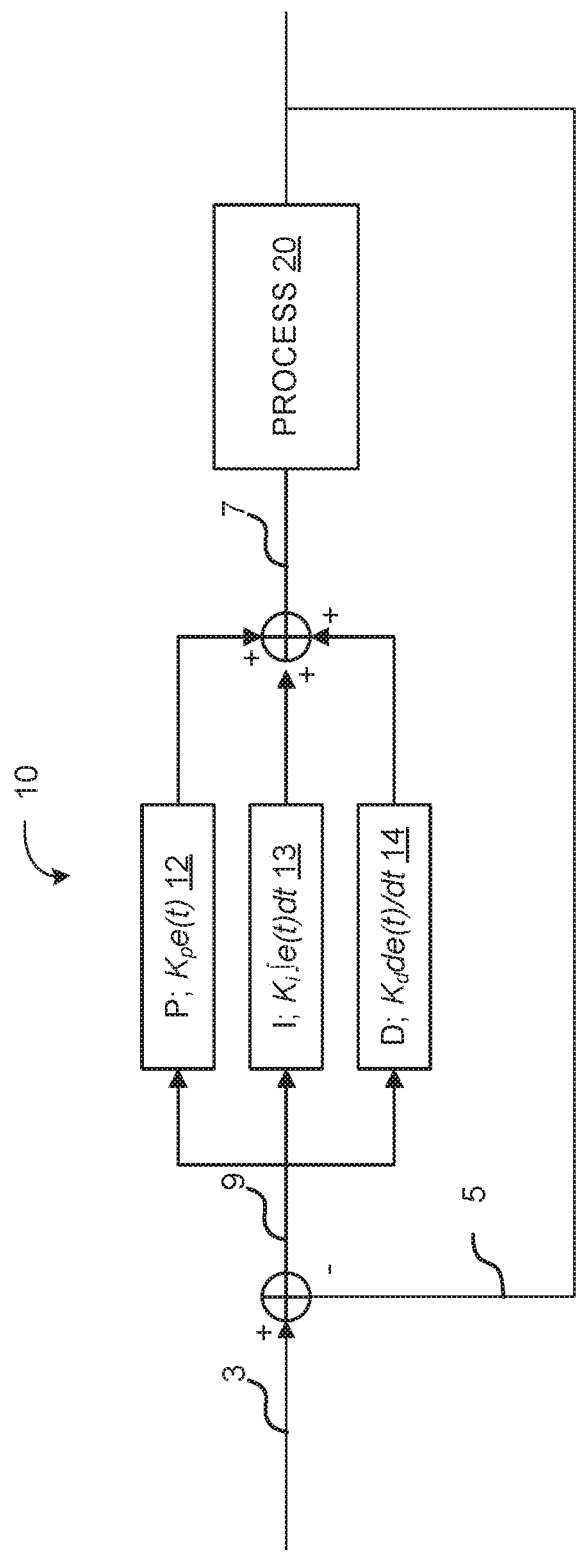
FIG. 1 illustrates an example of a servo system that can be used for actuator control.

It should be understood that the disclosed technology can be practiced with modification and alteration, and that the disclosed technology be limited only by the claims and the equivalents thereof.

DETAILED DESCRIPTION

Various examples of the technologies disclosed herein provide systems and methods for real-time setting of operational parameters for a servo control system used in an optical imaging system such as a sequencing system. Many imaging systems include a sample stage that holds a sample or other object to be imaged and an optical stage that includes the optics used for the imaging operations. Focusing operations involve moving the optical stage relative to the sample stage using an actuator to accomplish the movement. These imaging systems may be capable of operating in different modes of operation, and these different modes of operation may require different modes of actuation to be accomplished by the actuator. For example, a mode of operation involving focus model generation may require holding a sample stage at a fixed position relative to the optical stage for a period of time to acquire focus information, while sequencing operations may require fast focusing adjustments to maintain adequate throughput. In some applications, the systems and methods disclosed herein can be configured to detect a mode of operation of an imaging system during system operation, and to adjust operation of the servo system controlling the actuator to optimize servo control for the mode of operation. This can include, for example, adjusting operational parameters of the servo system such as gain amounts and filter values. As another example, this can include changing the feedback loop in the servo system.

Accordingly, sets of servo system parameters optimized for various modes of operation can be determined in advance and stored for recall during system operations. During operations, the system can determine a mode of operation, servo system parameters optimized for the determined mode of operation, and apply those servo system parameters to the servo system so that actuator control is optimized for the mode. This can be done in real time during imaging operations so that the imaging system does not need to be halted so that parameters can be loaded for mode changes. Likewise, different feedback mechanisms can be determined for the different modes of operation and these feedback mechanisms can also be selected to optimize the feedback approach for the servo controller. This can also be done in real time so that the imaging system does not need to be halted for changes to the servo system.

Before describing various example systems and methods in detail, it is useful to describe an example environment with which the systems and methods can be implemented. One such example environment is that of an image scanning system, such as that illustrated in FIG. 2. The example imaging scanning system may include a device for obtaining or producing an image of a region. The example outlined in FIG. 2 shows an example imaging configuration of a backlight design.

Figure 2:
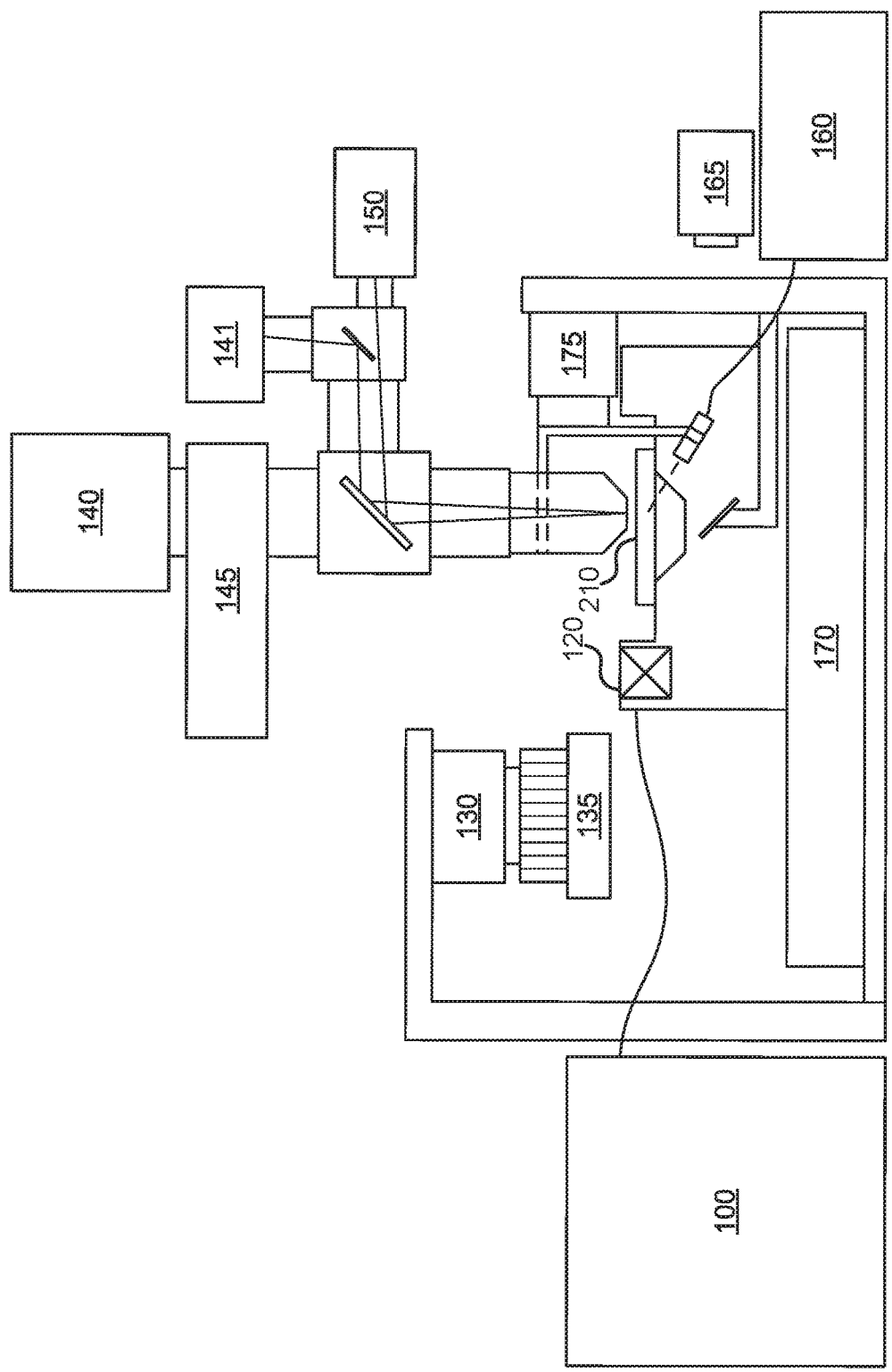
FIG. 2 illustrates a simplified block diagram of one example of an image scanning system with which systems and methods disclosed herein may be implemented.

As can be seen in the example of FIG. 2, subject samples are located on sample container 110, which is positioned on a sample stage 170 under an objective lens 142. Light source 160 and associated optics direct a beam of light, such as laser light, to a chosen sample location on the sample container 110. The sample fluoresces and the resultant light is collected by the objective lens 142 and directed to a photo detector 140 to detect the fluorescence. Sample stage 170 is moved relative to objective lens 142 to position the next sample location on sample container 110 at the focal point of the objective lens 142. Movement of sample stage 110 relative to objective lens 142 can be achieved by moving the sample stage itself, the objective lens, the entire optical stage, or any combination of the foregoing. Further examples may also include moving the entire imaging system over a stationary sample.

Fluid delivery module or device 100 directs the flow of reagents (e.g., fluorescent nucleotides, buffers, enzymes, cleavage reagents, etc.) to (and through) sample container 110 and waste valve 120. In some applications, the sample container 110 can be implemented as a flowcell that includes clusters of nucleic acid sequences at a plurality of sample locations on the sample container 110. The samples to be sequenced may be attached to the substrate of the flowcell, along with other optional components.

The system also comprises temperature station actuator 130 and heater/cooler 135 that can optionally regulate the temperature of conditions of the fluids within the sample container 110. Camera system 140 can be included to monitor and track the sequencing of sample container 110. Camera system 140 can be implemented, for example, as a CCD camera, which can interact with various filters within filter switching assembly 145, objective lens 142, and focusing laser/focusing laser assembly 150. Camera system 140 is not limited to a CCD camera and other cameras and image sensor technologies can be used.

Light source 160 (e.g., an excitation laser within an assembly optionally comprising multiple lasers) or other light source can be included to illuminate fluorescent sequencing reactions within the samples via illumination through fiber optic interface 161 (which can optionally comprise one or more re-imaging lenses, a fiber optic mounting, etc.). Low watt lamp 165, focusing laser 150, and reverse dichroic 185 are also presented in the example shown. In some applications focusing laser 150 may be turned off during imaging. In other applications, an alternative focus configuration can include a second focusing camera (not shown), which can be a quadrant detector, a Position Sensitive Detector (PSD), or similar detector to measure the location of the scattered beam reflected from the surface concurrent with data collection.

Although illustrated as a backlit device, other examples may include a light from a laser or other light source that is directed through the objective lens 142 onto the samples on sample container 110. Sample container 110 can be ultimately mounted on a sample stage 170 to provide movement and alignment of the sample container 110 relative to the objective lens 142. The sample stage can have one or more actuators to allow it to move in any of three directions. For example, in terms of the Cartesian coordinate system, actuators can be provided to allow the stage to move in the X, Y and Z directions relative to the objective lens. This can allow one or more sample locations on sample container 110 to be positioned in optical alignment with objective lens 142.

A focus (z-axis) component 175 is shown in this example as being included to control positioning of the optical components relative to the sample container 110 in the focus direction (typically referred to as the z axis, or z direction). Focus component 175 can include one or more actuators physically coupled to the optical stage or the sample stage, or both, to move sample container 110 on sample stage 170 relative to the optical components (e.g., the objective lens 142) to provide proper focusing for the imaging operation. For example, the actuator may be physically coupled to the respective stage such as, for example, by mechanical, magnetic, fluidic or other attachment or contact directly or indirectly to or with the stage. The one or more actuators can be configured to move the stage in the z-direction while maintaining the sample stage in the same plane (e.g., maintaining a level or horizontal attitude, perpendicular to the optical axis). The one or more actuators can also be configured to tilt the stage. This can be done, for example, so that sample container 110 can be leveled dynamically to account for any slope in its surfaces.

Focusing of the system generally refers to aligning the focal plane of the objective lens with the sample to be imaged at the chosen sample location. However, focusing can also refer to adjustments to the system to obtain a desired characteristic for a representation of the sample such as, for example, a desired level of sharpness or contrast for an image of a test sample. Because the usable depth of field of the focal plane of the objective lens may be very small (sometimes on the order of 1 µm or less), focus component 175 closely follows the surface being imaged. Because the sample container is not perfectly flat as fixtured in the instrument, focus component 175 may be set up to follow this profile while moving along in the scanning direction (typically referred to as the y-axis).

The light emanating from a test sample at a sample location being imaged can be directed to one or more detectors 140. Detectors can include, for example a CCD camera. An aperture can be included and positioned to allow only light emanating from the focus area to pass to the detector. The aperture can be included to improve image quality by filtering out components of the light that emanate from areas that are outside of the focus area. Emission filters can be included in filter switching assembly 145, which can be selected to record a determined emission wavelength and to cut out any stray laser light.

In various examples, sample container 110 can include one or more substrates upon which the samples are provided. For example, in the case of a system to analyze a large number of different nucleic acid sequences, sample container 110 can include one or more substrates on which nucleic acids to be sequenced are bound, attached or associated. In various examples, the substrate can include any inert substrate or matrix to which nucleic acids can be attached, such as for example glass surfaces, plastic surfaces, latex, dextran, polystyrene surfaces, polypropylene surfaces, polyacrylamide gels, gold surfaces, and silicon wafers. In some applications, the substrate is within a channel or other area at a plurality of locations formed in a matrix or array across the sample container 110.

One or more controllers (not illustrated) can be provided to control the operation of a scanning system, such as the example scanning system described above with reference to FIG. 2. The controller can be implemented to control aspects of system operation such as, for example, focusing, stage movement, and imaging operations. In various applications, the controller can be implemented using hardware, software, or a combination of the foregoing. For example, in some implementations the controller can include one or more CPUs or processors with associated memory. As another example, the controller can comprise hardware or other circuitry to control the operation. For example, this circuitry can include one or more of the following: field programmable gate array (FPGA), application specific integrated circuit (ASIC), programmable logic device (PLD), complex programmable logic device (CPLD), a programmable logic array (PLA), programmable array logic (PAL) or other similar processing device or circuitry. As yet another example, the controller can comprise a combination of this circuitry with one or more processors.

Although the systems and methods may be described herein from time to time in the context of this example system, this is only one example with which these systems and methods might be implemented. After reading this description, one of ordinary skill in the art will understand how the systems and methods described herein can be implemented with this and other scanners, microscopes and other imaging systems.

As the example described above with reference to FIG. 2 illustrates, focusing operations can be an important part of the imaging process. In some applications, a focus model can be prepared for the imaging operation and the focus model can then be used to properly position the objective lens relative to the samples during imaging operations. Generally, in operation, a focus beam generated by a focusing laser is reflected off of the sample location to measure the required focus, and the sample stage is moved relative to the optical stage to focus the optical stage onto a current sample location.

The movement of the sample stage relative to the optical stage for focusing model generation and for proper in-focus position during imaging is generally described as movement along the z-axis or in the z direction. The terms "z-axis" and "z direction" are intended to be used consistently with their use in the art of microscopy and imaging systems in general, in which the z-axis refers to the focal axis. Accordingly, a z-axis translation results in increasing or decreasing the length of the focal axis. A z-axis translation can be carried out, for example, by moving a sample stage relative to an optical stage (e.g., by moving the sample stage or an optical element or both). As such, z-axis translation can be carried out by driving an objective lens, the optical stage, or the sample stage, or a combination of the foregoing, any of which can be driven by actuating one or more servos or motors or other actuators that are in functional communication with the objective lens or the sample stage or both. In various examples, the actuators can be configured to tilt the sample stage relative to the optical stage to, for example, effectively level the sample container on a plane perpendicular to the optical imaging axis. Where this dynamic tilting is performed to effectively level the sample locations on the sample container, this can allow the sample container to be moved in the x and y directions for scanning with little or no movement in the z-axis required. Although this disclosure adopts the terminology z-axis and the direction, it should be understood that this is done for clarity of description and consistency with conventional terminology. The principles disclosed herein are not dependent on these mnemonics, and other terminology can be used to describe movement in the x, y and z directions.

In various examples an actuator can be used to position the sample stage relative to the optical stage by repositioning either the sample stage or the optical stage (or parts thereof), or both to achieve the desired focus setting. In some examples, piezoelectric actuators can be used to move the desired stage. In other examples, a voice coil actuator can be used to move the desired stage. In some applications, the use of a voice coil actuator can provide reduced focusing latency as compared to its piezoelectric counterparts. Where a voice coil actuator is used, coil size may be chosen as a minimum coil size necessary to provide the desired movement such that the inductance in the coil can also be minimized. Limiting coil size, and therefore limiting its inductance, provides quicker reaction times and requires less voltage to drive the actuator.

For focus model generation, it is often desired to maintain the optical system with as little movement as possible for a period of time while the proper focus is determined for a sample location. For example, in some applications, it may be required to hold the position of the objective lens relative to the sample container to within a few nanometers of target position. In contrast, imaging operations require relatively fast scanning of the DNA clusters in the surface of the sample container. The image acquisition scanning speed is driven by instrument run time requirements and creates a bandwidth requirement of the focusing system and z-stage. This generally involves a control system having a high bandwidth to enable high-quality imaging at high throughput rates, which requires rapid movement of the objective lens relative to the sample container to the precise in-focus location. However, this is at odds with control system requirements for focus model generation, where the objective may be to hold the optical system as still as possible at a target location. Accordingly, the technology disclosed herein may be implemented to provide real-time switching of the z-stage controller depending on the current operational mode. This technology can be implemented to effectively break this trade-off constraint between holding during focus model generation and high-speed movement during imaging by enabling the application of a first control system optimized for holding and a second control system optimized for fast imaging and providing a mechanism for switching between these control systems depending on the current mode.

Figure 3:
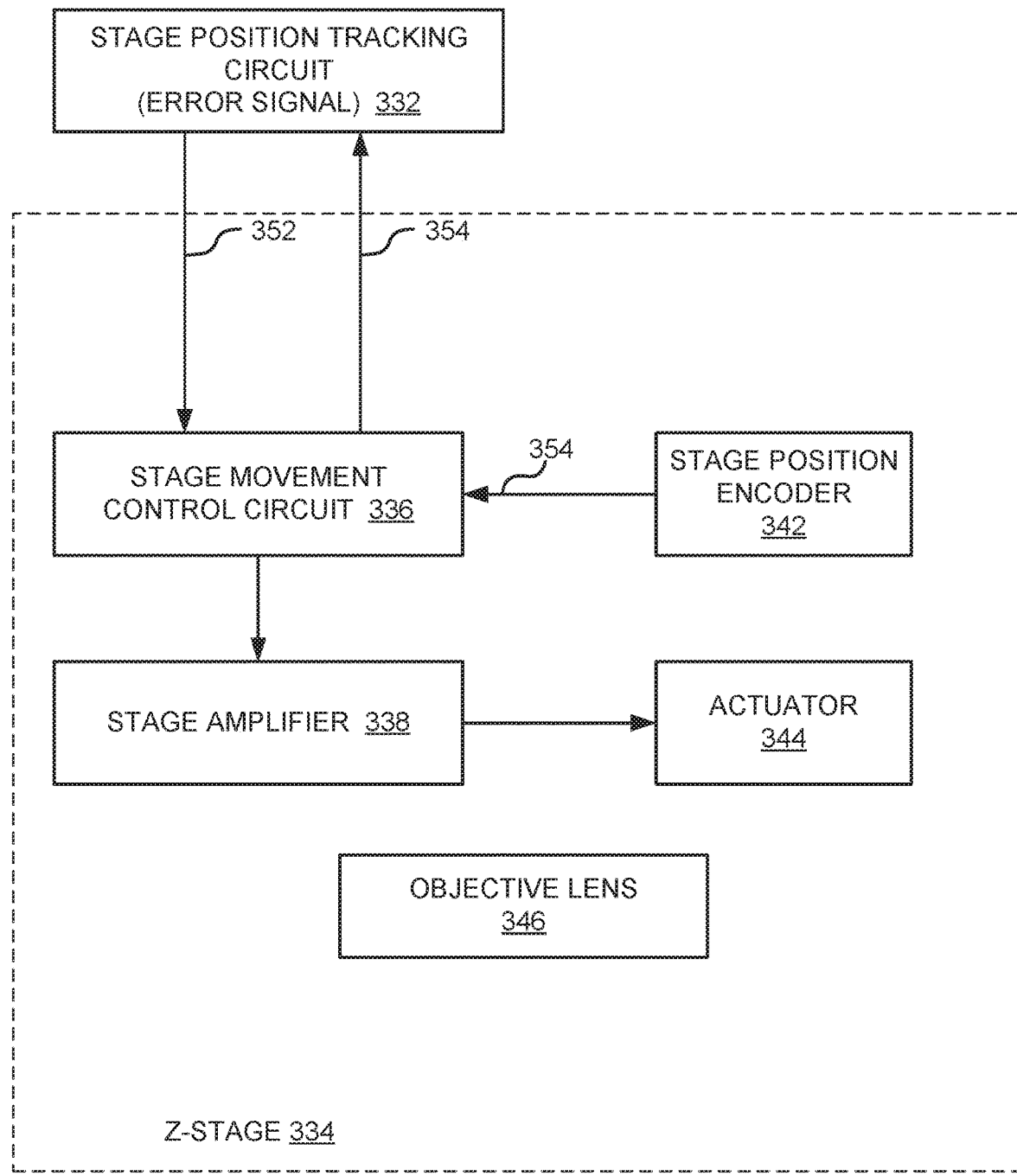
FIG. 3 is a block diagram illustrating an example focus control system for focus operations in accordance with one example of the systems and methods described herein.

FIG. 3 is a block diagram illustrating an example focus control system for focus operations in accordance with one application of the systems and methods described herein. This example focus control system includes focus tracking circuitry 332 that is configured to determine the current focus settings that are used to generate the drive signal that drives the focus tracking feedback loop in the z-stage 334. As illustrated in the example of FIG. 3, commands 352, based on the focus settings difference, are fed to the z-stage 334 to control movement of the z-stage 334.

In this example, the z-stage 334 is configured to move the objective lens 346 (e.g., objective lens 142). Actuator 344 moves the optical stage, and in particular the objective lens 346, in response to the drive signal provided by the z-stage amplifier 338. As noted above, actuator 344 can include a piezoelectric actuator, a voice coil actuator, a motor, or other like actuators. An position encoder 342 provides information about the actuator position and its movement. This encoder information 354 can be fed back through the z-stage controller 336 to focus tracking circuitry 332 and can be used in determining the error signal.

Controllers used to control the movement can be implemented using a PID controller with feedforward, including both position and velocity controllers. They can include proportional, integral and derivative control for both the error signal and the feedforward control branches. Some examples can also include additional filters and trajectory generation that can be used to improve the stability of the system depending on the use cases.

Figure 4:
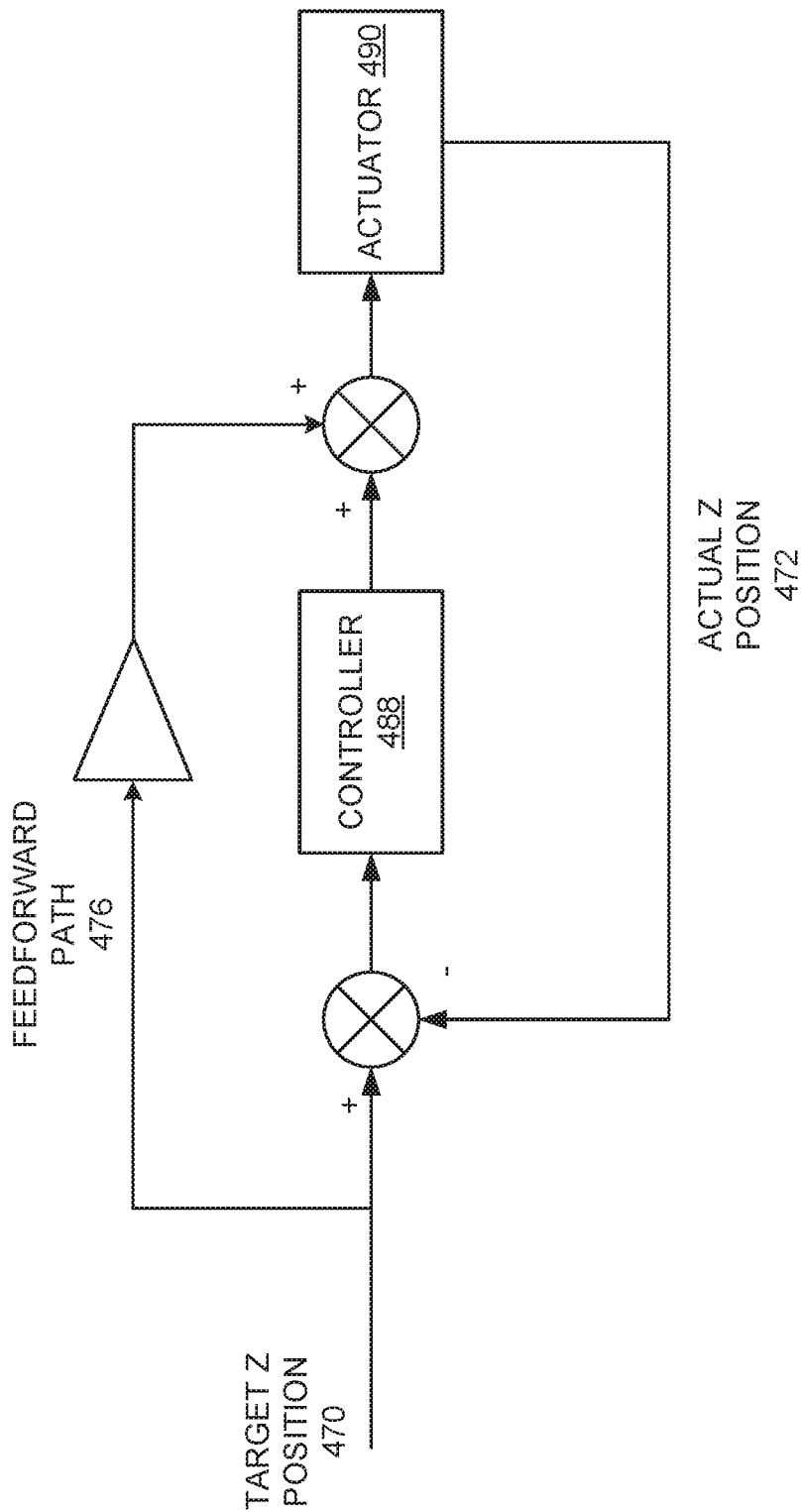
FIG. 4 is a diagram illustrating an example architecture for a z-stage controller in accordance with one example of the systems and methods described herein.

FIG. 4 is a diagram illustrating an example architecture for a z-stage controller in accordance with one example of the systems and methods described herein. This example controller incorporates both feedforward and feedback control to generate the drive signal to control the stage actuator. In some examples, this can be implemented as a proportional, integral and derivative (PID) control for either or both the error signal and the feedforward control branches of the control system. As illustrated in this example, the difference between the target focus setting and the actual focus setting are computed and fed to control block 488. Position information is also sent via feedforward path 476 and added to the output signal of control block 488. This output signal from drive circuitry within the control block 488 provides the control output signal, which is used to drive actuator 490. As shown, the magnitude of the difference between the target focus position and the actual position is provided via the feedforward path 476 to adjust the control output signal.

Figure 5:
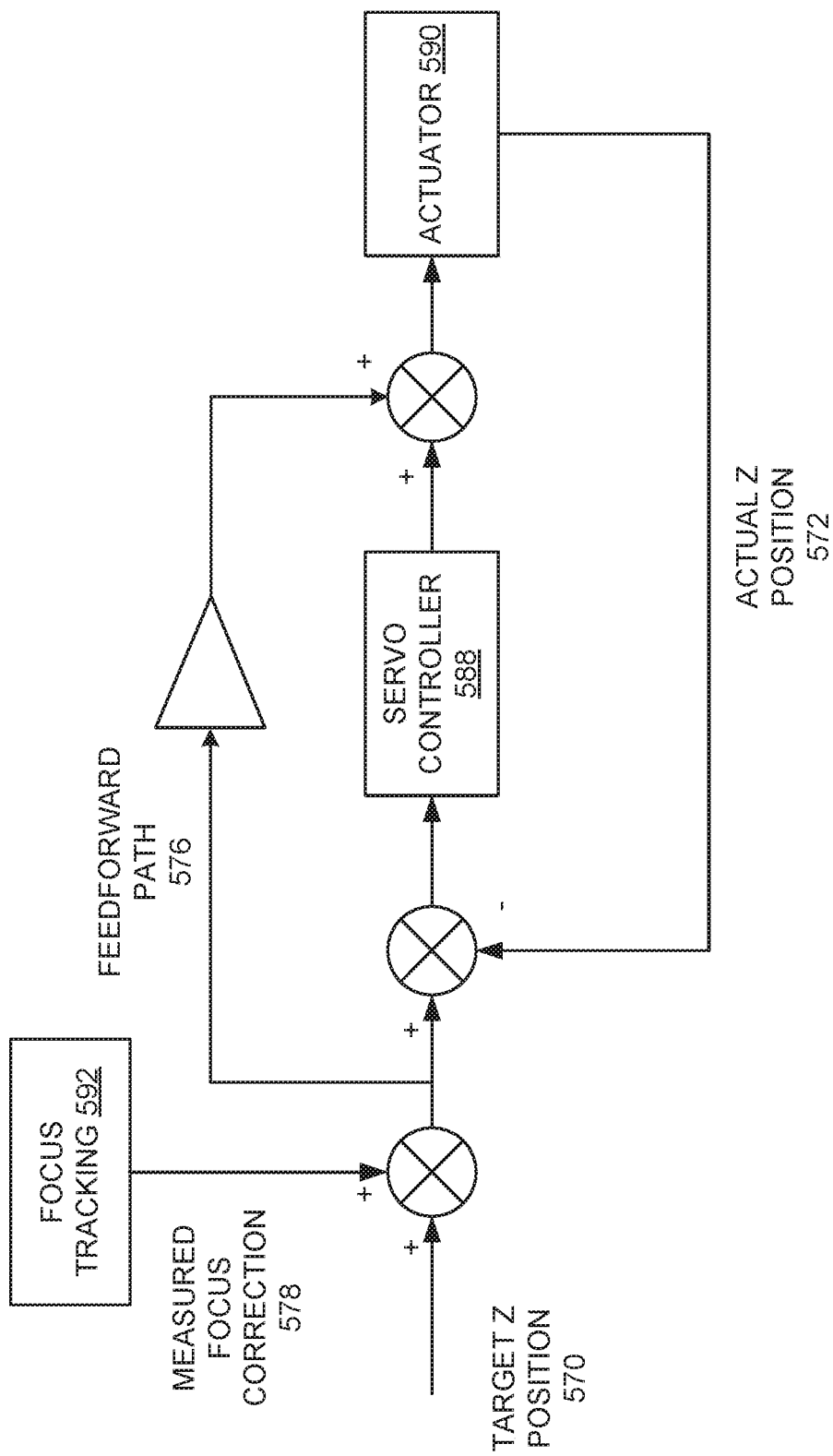
FIG. 5 is diagram illustrating another example architecture for a z-stage controller in accordance with one example of the systems and methods described herein.

FIG. 5 is diagram illustrating another example architecture for a z-stage controller in accordance with one example of the systems and methods described herein. This example also incorporates feedback and feedforward control. In operation, the target focus setting (e.g., target z position 570) is used to command the position of the stage. The target z position 570 is provided to servo controller 588, which determines the drive signal needed to command actuator 590 to position the stage. Servo controller 588 may also include drive circuitry to generate the drive signal. The drive signal determination is made using the magnitude of the difference between the target focus setting (target z position 570) and the current focus setting (actual z position 572) which can be provided, for example, by actuator 590. In this example, as well as in the previous example, the drive signal used to drive the actuator is adjusted by the signal from the feedforward control path 576.

However, in the example of FIG. 5, a measured focus correction signal 578 is also generated by focus tracking circuitry 592, which can be active, for example, during a scanning mode. In this case, the correction information can be determined, for example, using measured focus correction information. The correction information in this example is added to the commanded stage position to adjust the drive signal according to the slope of the change in the focus setting for scanning operations. For example, this feedback path can be switched on or enabled when the imaging system is in the scanning mode to provide this correction information to the servo controller. In some applications, the system can be controlled such that the servo controller's position loop may be open, or partially open when the system is in the scan mode as the focus tracking circuitry 592 provides real time feedback relative to a moving target.

Figure 6:
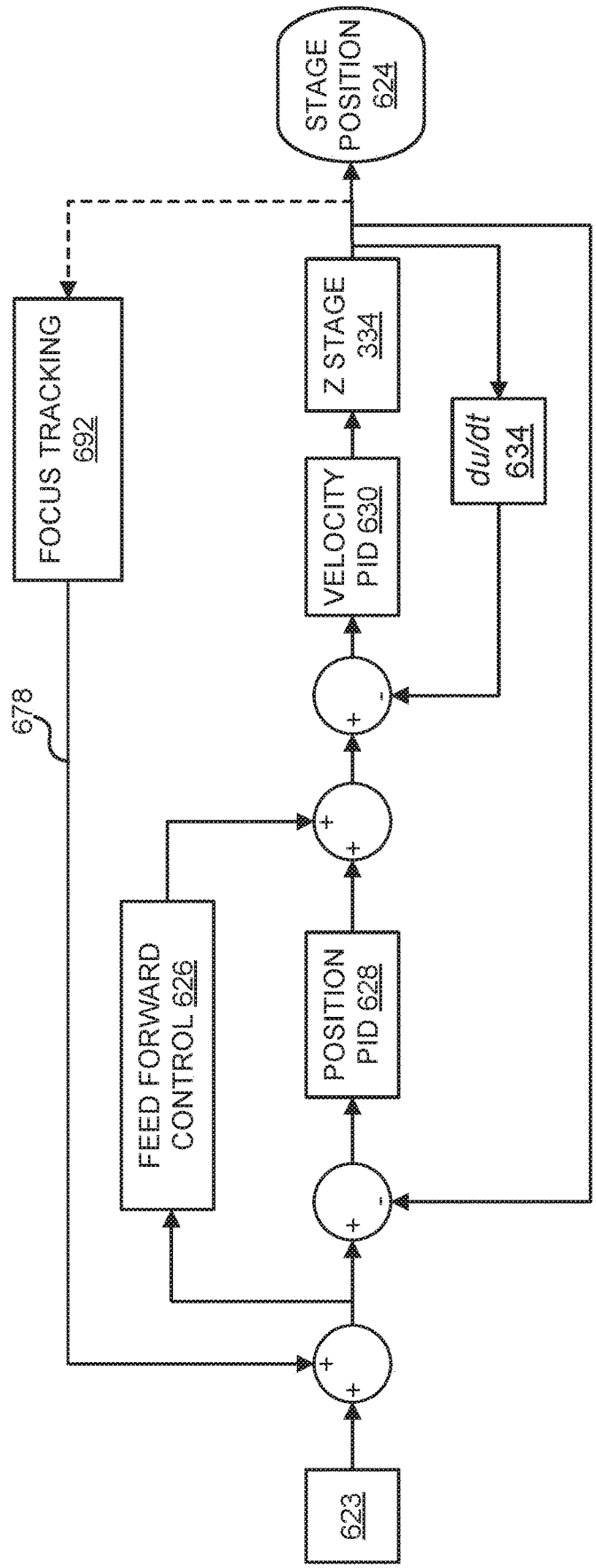
FIG. 6 is a diagram illustrating another example controller using feedback and feedforward control with focus tracking input in accordance with one example of the systems and methods described herein.

FIG. 6 is a diagram illustrating another example servo controller using feedback and feedforward control with focus tracking input in accordance with one example of the systems and methods described herein. The target imaging distance 623 is provided as an input to the control system to generate a stage position signal to control the z-stage (e.g., z-stage 334). This system also includes a feedforward control 626 in addition to a position control 628. The feedforward path can provide faster response by taking the command around the generally slower position loop, directly to the velocity loop (described below). When the position changes are more dramatic, the feed forward control 626 forward path forwards that change to the velocity PID 630 for faster system response than typically may otherwise be achieved by relying solely on the position PID 628. Velocity control 630, which may also be implemented as a PID controller, is implemented in this example within the position loop. Feedback 634 for the velocity loop is in the form of a derivative of the determined position. Constant position errors in some instances can be small enough that the position PID 628 alone does not generate enough torque to overcome the static friction of the system. In such cases, velocity PID 630 provides additional gain to overcome this friction. Force to velocity has a 90-degree phase shift, which allows higher gains for better profile tracking and holding.

As with the example of FIG. 5, this example includes measured focus correction feedback from focus tracking circuitry 692. As in the example of FIG. 5, measured focus correction signal 678 may be generated by focus tracking circuitry 692. This correction information in this example is added to the commanded stage position to adjust the drive signal according to the slope of the change in the focus setting for scanning operations. As is the case in the example of FIG. 5, in some applications, the system can be controlled such that the servo controller's position loop may be open, or partially open when the system is in the scan mode as the focus tracking circuitry 592 provides real time feedback relative to a moving target.

Figure 7:
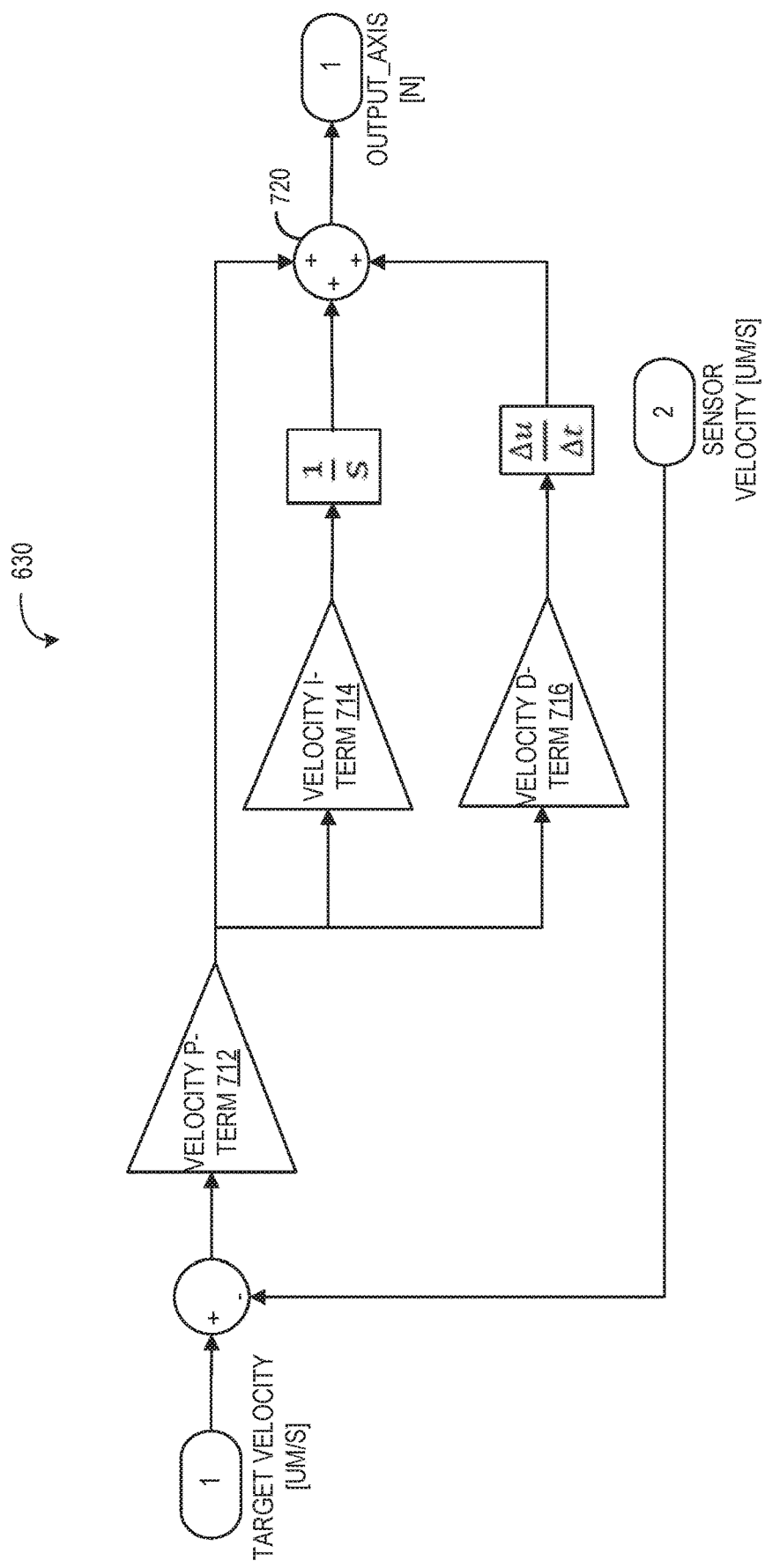
FIG. 7 is a diagram illustrating a velocity controller in accordance with one example of the systems and methods described herein.

FIG. 7 is a diagram illustrating a velocity controller in accordance with one example of the systems and methods described herein. This illustrates one example implementation of a velocity PID controller 630 that can be used to provide a velocity loop within a servo controller. This example includes gain stages for the proportional term 712, the integral term 714 and the derivative terms 716. The gains are summed by summing circuit 722 provide the control output for the velocity PID controller 630.

As noted, the various applications of the systems and methods described herein can be employed to provide real-time mode detection and control parameter switching to optimize servo control or operational parameters based on the detected current mode of the operating instrument. For example, in the case of a sequencing instrument, systems and methods described herein may be implemented to detect whether the sequencing instrument is in a focus model mode or a sequencing mode, determine the correct set of operating parameters for the z-stage servo controller that are defined as suitable for that mode of operation, and updating the servo controllers parameters with the specific parameters defined for that mode of operation. Any of a number of servo controller parameters can be defined and selected to optimize the servo operation for the detected mode. For example, different sets of parameters, such as for example integral gains, derivative gains, feedforward and filter cutoff frequencies, and other like parameters, can be defined for various modes of operation and implemented for the desired mode of operation. For example, high loop gains can be implemented to achieve responsive performance and help reject disturbances. However, high loop gains can also cause instability.

Table 1 illustrates an example set of parameters that can be defined for a holding mode and a scanning mode in a sequencing instrument.

TABLE 1

| Mode | Example Parameters | | | | |
|---|---|---|---|---|---|
| | Relative Move | Trajectory Generator | PPGain | VPGain | Control Version |
| MemID | 0x06010800 | 0x06010300 | 0x07000300 | 0x07000307 | |
| Holding | 0 | 1 | 800 | 4.00E−04 | 5.0 |
| Scanning | 1 | 0 | 200 | 9.00E−04 | 5.8 |

In this example, predefined values for position loop gain and velocity loop gain are provided for a holding mode and a scanning mode. The relative move implementation is intended to reduce or minimize error in a current position because the local controller has the most current measurement of the position of the stage actuator, and reducing or minimizing latency is important for scanning operations. Also, many scanning operations rely only on relative moves. The trajectory generator implementation, on the other hand, is useful for focus model generation. Focus model generation and generally relies on knowledge of the absolute position of the z-position to calibrate the focusing system. However, latency is generally not as important for focus calibration and absolute positioning can be used. Accordingly, in the example provided in table 1, gains for the position loop are relatively higher for holding operations than they are for scanning operations, whereas gains for the velocity loop are lower than these gains may be set for scanning operations. This example of table 1 does not illustrate every parameter that may be adjusted, and the systems and methods disclosed herein can be extended to predefined additional parameters in the focusing servo system.

Figure 8:
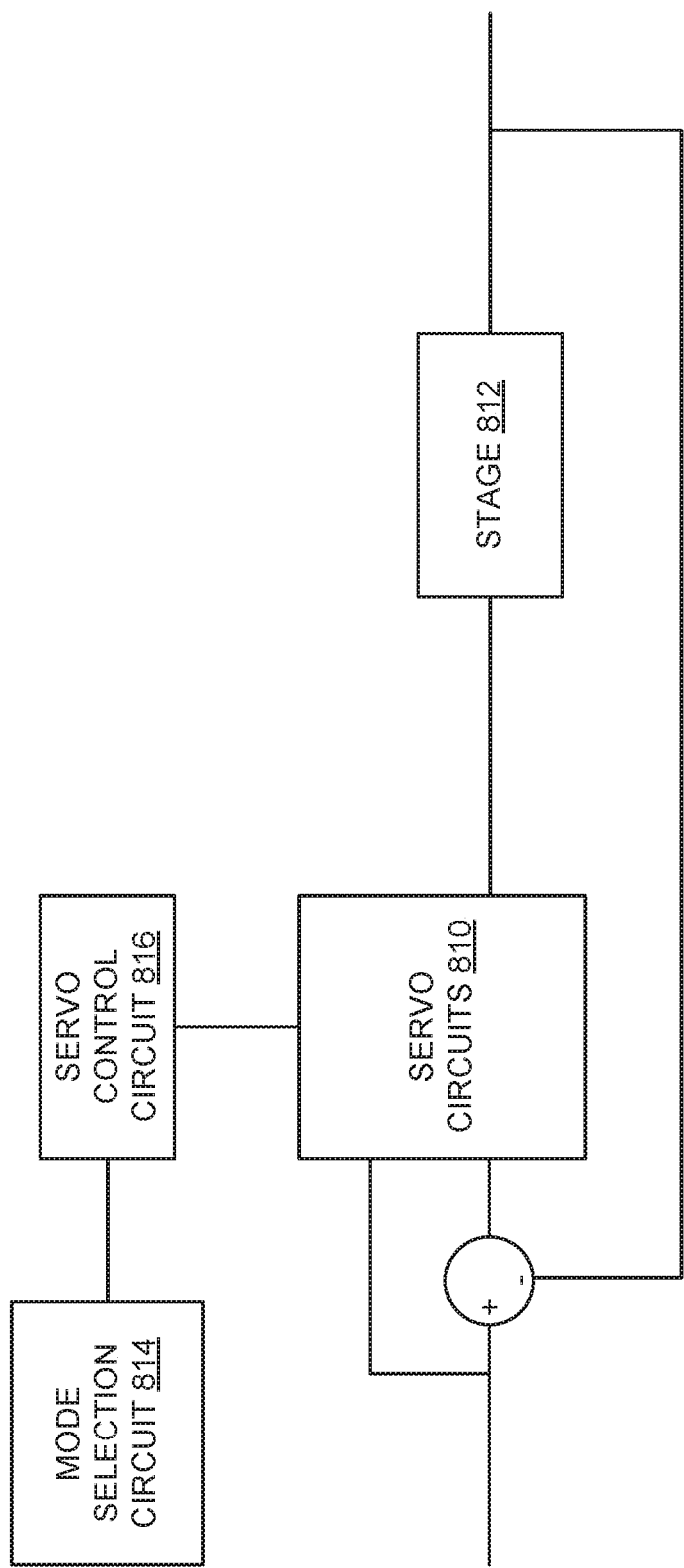
FIG. 8 is a diagram illustrating an example implementation of controller switching in accordance with one application of the systems and methods described herein.

FIG. 8 is a diagram illustrating an example implementation of controller switching in accordance with one application of the systems and methods described herein. The illustrated example includes a mode selection circuit 814 and a servo control circuit 816 that can be implemented to control or adjust the operational parameters or the feedback mechanism, or combinations thereof, of one or more servo controllers 810 that are controlling the movement of a stage 812. Mode selection circuit 814 may be implemented in the sequencing instrument (or other instrument to which these systems and methods may be applied) to select the operational mode, including the selection of operational parameters and feedback mechanisms for the servo controller. For example, in the case of the example scenario using a scanning mode and a focus model generation mode, mode selection circuit 814 can be implemented to place the sequencing instrument into either of these modes based on the current operation of the imaging system. Mode selection circuit 814 may comprise independent circuitry, or it may be part of the controller used to control operation of the scanning system (such as the controller described above with reference to FIG. 1).

Information regarding the operational mode of the system is provided to servo control circuit 816. Servo control circuit 816 detects the operational mode of the instrument and selects the appropriate servo controller parameters or feedback mode (or both) based on the operational mode of the system. Servo control circuit 816 may be further implemented to set the affected parameters for the one or more servo loops that make up servo circuits 810. In the case of selecting appropriate servo controller parameters, these parameters can be stored in registers or other memory and the appropriate parameter or sets of parameters retrieved based on the operating mode of the system. In the case of adjusting the feedback mechanism, servo control circuit 816 can provide switching or control to enable feedback from the appropriate sources such as, for example, from focus tracking circuitry.

Figure 9:
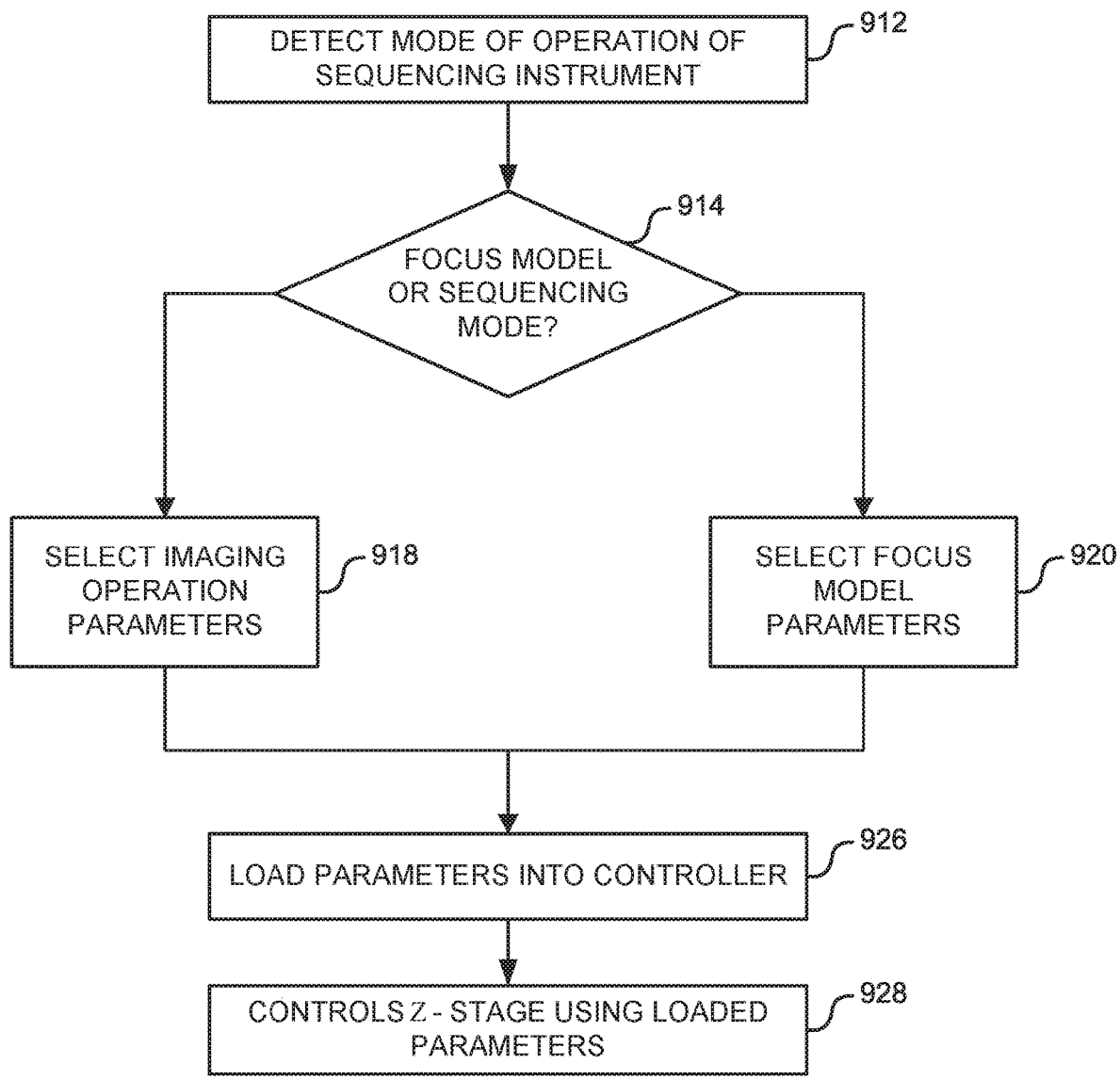
FIG. 9 illustrates a process for servo controller design switching in accordance with one application of the systems and methods described herein.

FIG. 9 illustrates a process for servo controller design switching in accordance with one application of the systems and methods described herein. In this example, at operation 912, the servo mode control circuit (e.g., servo control circuit 816) determines the operational mode of the sequencing instrument. In some applications, this determination can be made by receiving a signal from a controller or other apparatus of the sequencing instrument that indicates to the servo motor control circuit the current state of the machine. For example, a signal path can provide different signal levels to indicate the state of the sequencing instrument. As another example, the signal path can provide a series of bits or bytes indicating the current mode of operation.

At operation 916, the servo motor control circuit determines the mode of operation of the sequencing instrument. In accordance with the example described above, at this step the servo motor control circuit can determine whether the instrument is operating in a focus model generation mode or in a sequencing mode. If the servo motor control circuit determines that the instrument is operating in a sequencing mode, at operation 918 the servo motor control circuit selects parameters optimized for controlling the z-stage for imaging operations. In applications in which the feedback mechanism is also selected (or alternatively selected), the servo motor control circuit may also enable the feedback path from focus tracking circuitry when the instrument is operating in the sequencing mode. If, on the other hand, the servo motor control circuit determines that the instrument is operating in a focus model generation mode, at operation 920 the servo motor control circuit selects servo control parameters optimized for controlling the z-stage in this mode. In further applications, additional operational modes can be detected and parameters for these modes selected.

At operation 926 the selected servo control parameters are loaded into the appropriate loop or loops of the servo controller. At operation 928 the servo system controls the z-stage using the loaded parameters and the appropriate feedback mechanisms.

Figure 10:
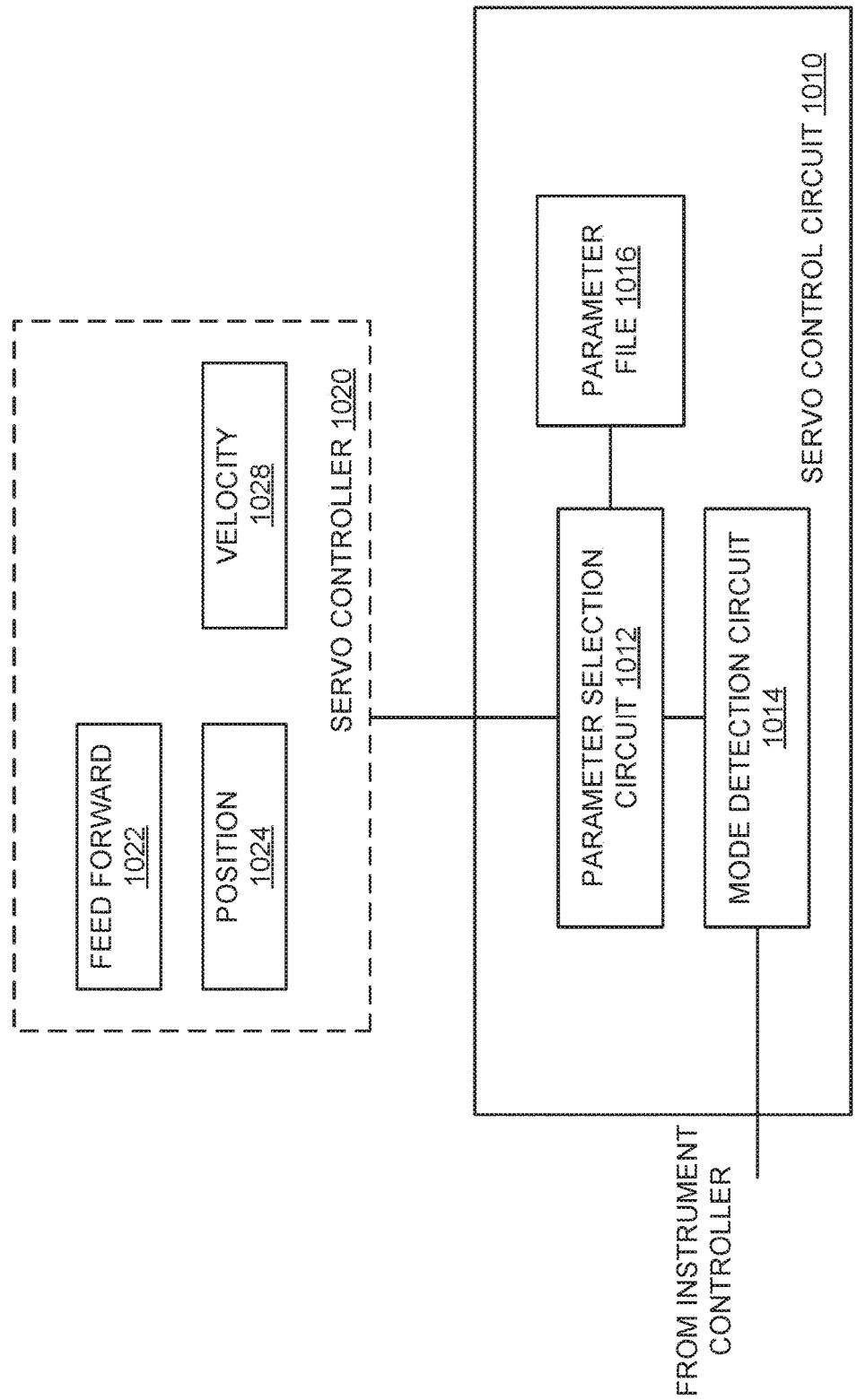
FIG. 10 is a diagram illustrating an example implementation of a Servo control circuit in accordance with one application of the systems and methods described herein.

FIG. 10 is a diagram illustrating an example implementation of a Servo control circuit in accordance with one application of the systems and methods described herein. In this example, a Servo control circuit 1010 controls the application of operational parameters to servo controller 1020. Servo controller 1020 includes feedforward control 1022, a position control loop 1024 and a velocity control loop 1028. Depending on the servo system, the servo controller can include additional or other control loops. These control loops can be implemented to operate at different performance levels depending on operational parameters such as gain amounts, filter values, and so on.

The example servo control circuit 1010 includes a mode detection circuit 1014, a parameter selection circuit 1012 and a parameter file 1016. Mode detection circuit 1014 receives information from the instrument controller that mode detection circuit 1014 can use to determine the operational mode of the instrument. In some applications, the instrument may output a digital or analog signal indicating the current operational mode of the instrument. For example, in the case of a sequencing instrument, the operational modes can include mode such as a focus model generating mode and a sequencing mode. As another example, a bit or group of bits, or a flag can be set indicating the mode, and the bit or bits read by mode detection circuit 1014 to determine the operational mode.

Once the operational mode is determined, parameter selection circuit 1012 selects the parameter set corresponding to the detected operational mode. In the illustrated example, the parameter sets can be stored in memory or other like storage, such as in a parameter file 1016, and retrieved by parameter selection circuit 1012. Parameter selection circuit 1012 loads the parameters into a controller or controllers for the appropriate loops of servo controller 1020. When the mode of the instrument is changed, this change can be detected by mode detection circuit 1014 and new parameters selected and loaded into the appropriate control loops of servo controller 1020. In some applications, parameter set loading can occur in real-time (but may still be dependent upon system latencies or other delays) so that the servo parameters can be changed on the fly.

The set or sets of parameters identified for servo operation can be further optimized for the given instrument with which the servo system is implemented. For example, different instruments can have different structural or other characteristics that can respond to and interact with the control system. This interaction may result in vibrations, harmonic movement, or other instabilities that may adversely impact system performance or that could even cause failures. Accordingly, the parameters can be optimized for the instrument by a manual refinement process or by using automated tools to create a custom implementation of parameters for the operational modes, such as holding and scanning, for a given instrument.

In some applications, the process of optimizing parameters of the sets of parameters for a given instrument can be accomplished by operating the instrument and scanning through a predetermined range of values of one or more of the control parameters while measuring the stability of the control system during each operation. In some cases, each control parameter can be measured and optimized individually, while in other cases, multiple control parameters can be systematically adjusted to identify the optimal settings for a combination of control parameters. During the calibration process, rest time can be inserted between operation at the various control parameter settings such that instabilities induced by one parameter setting do not contaminate measurements at subsequent parameter settings. For a given system, the optimal operating point may be chosen, for example, as a set of parameters that introduces minimum instability. The optimal operating point may present itself as a minimum in the variability in performance, with a generally quadratic relation for which an operational minimum can be determined computationally and saved as a custom implementation file for a given instrument.

Although examples disclosed herein refer to sets of parameters that can be used to optimize a servo system for particular modes of operation, optimization may not achieve perfectly ideal operation. A set of parameters intended to optimize operation in a given mode may achieve operating levels that are as high as possible given constraints of the operating parameters, system constraints, and real-world conditions under which the system is operating. Optimization may also be subject to design trade-offs and the amount of optimization achieved may be based on an appropriate level of operation as determined by system designers weighing these trade-offs.

As used herein, a circuit might be implemented utilizing any form of hardware, software, or a combination thereof. For example, one or more processors, controllers, ASICs, PLAs, PALs, CPLDs, FPGAs, logical components, software routines or other mechanisms might be implemented to make up a circuit. In implementation, the various circuits described herein might be implemented as discrete circuits or the functions and features described can be shared in part or in total among one or more circuits. In other words, the various features and functionality described herein may be implemented in any given application and can be implemented in one or more separate or shared circuits in various combinations and permutations. Even though various features or elements of functionality may be individually described or claimed as separate circuits, one of ordinary skill in the art will understand that these features and functionality can be shared among one or more common circuits, and such description shall not require or imply that separate circuits are required to implement such features or functionality.

Figure 11:
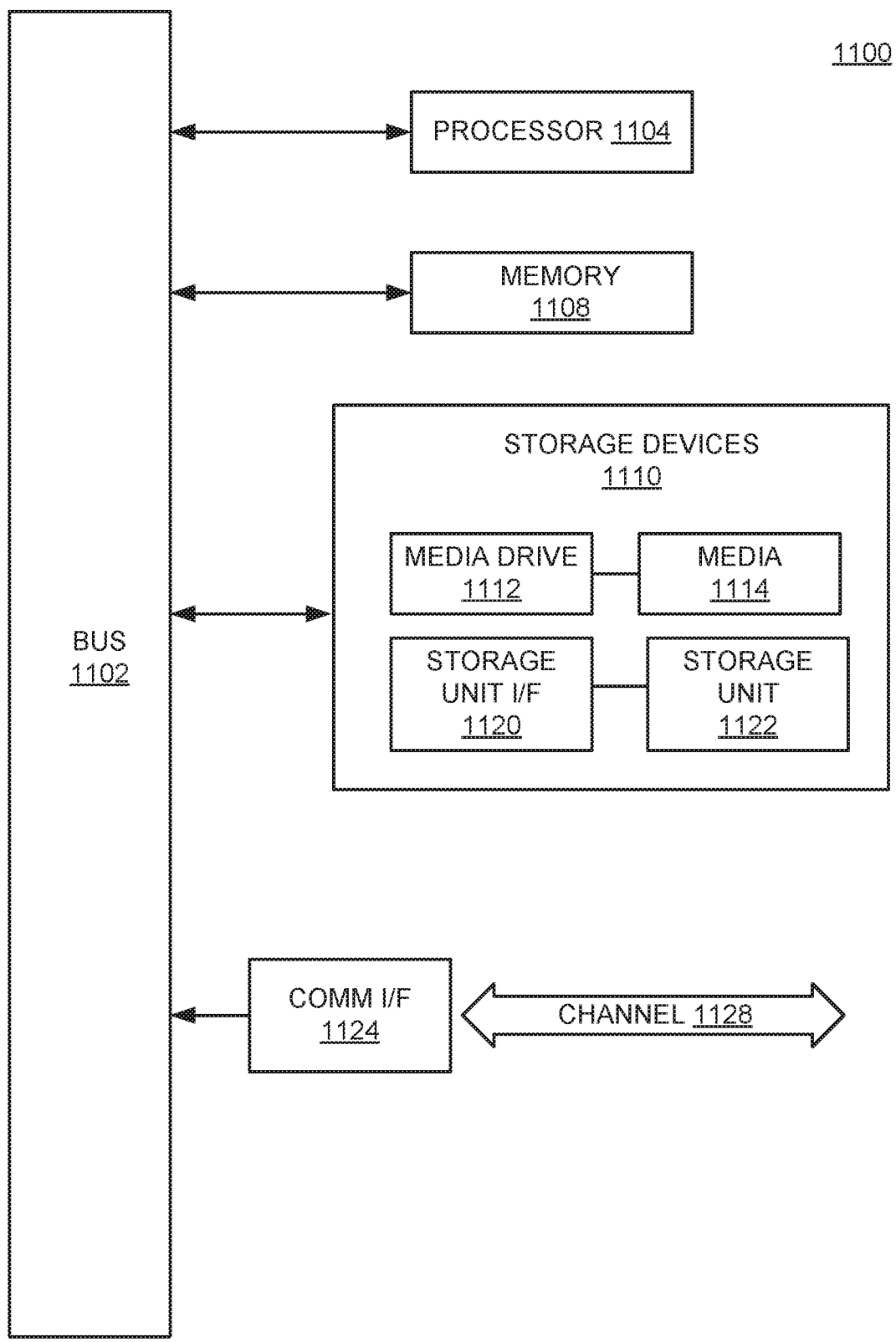
FIG. 11 illustrates an example circuit that may be used to implement various components of the disclosed technology.

As described herein, system controllers, servo controllers and other components of the systems and methods described herein can be implemented as circuits. Where circuits are implemented in whole or in part using software, in one implementation, these software elements can be implemented to operate with a computing or processing system capable of carrying out the functionality described with respect thereto. One such example computing system is shown in FIG. 11. Various examples are described in terms of this example-computing system 1100. After reading this description, it will become apparent to a person skilled in the relevant art how to implement the technology using other computing systems or architectures.

Referring now to FIG. 11, computing system 1100 may represent, for example, computing or processing capabilities found within desktop, laptop and notebook computers; hand-held computing devices (smart phones, cell phones, palmtops, tablets, etc.); mainframes, supercomputers, workstations or servers; or any other type of special-purpose or general-purpose computing devices as may be desirable or appropriate for a given application or environment. Computing system 1100 might also represent computing capabilities embedded within or otherwise available to a given device. For example, a computing system might be found in other electronic devices such as, for example, digital cameras, navigation systems, cellular telephones, portable computing devices, modems, routers, WAPs, terminals and other electronic devices that might include some form of processing capability.

Computing system 1100 might include, for example, one or more processors, controllers, control modules, or other processing devices, such as a processor 1104. Processor 1104 might be implemented using a general-purpose or special-purpose processing engine such as, for example, a microprocessor (whether single-, dual- or multi-core processor), signal processor, graphics processor (e.g., GPU) controller, or other control logic. In the illustrated example, processor 1104 is connected to a bus 1102, although any communication medium can be used to facilitate interaction with other components of computing system 1100 or to communicate externally.

Computing system 1100 might also include one or more memory modules, simply referred to herein as main memory 1108. For example, in some implementations random access memory (RAM) or other dynamic memory, might be used for storing information and instructions to be executed by processor 1104. Main memory 1108 might also be used for storing temporary variables or other intermediate information during execution of instructions to be executed by processor 1104. Computing system 1100 might likewise include a read only memory ("ROM") or other static storage device coupled to bus 1102 for storing static information and instructions for processor 1104.

The computing system 1100 might also include one or more various forms of information storage mechanism 1110, which might include, for example, a media drive 1112 and a storage unit interface 1120. The media drive 1112 might include a drive or other mechanism to support fixed or removable storage media 1114. For example, a hard disk drive, a floppy disk drive, a magnetic tape drive, an optical disk drive, a CD or DVD drive (R or RW), a flash drive, or other removable or fixed media drive might be provided. Accordingly, storage media 1114 might include, for example, a hard disk, a floppy disk, magnetic tape, cartridge, optical disk, a CD or DVD, or other fixed or removable medium that is read by, written to or accessed by media drive 1112. As these examples illustrate, the storage media 1114 can include a computer usable storage medium having stored therein computer software or data.

In alternative implementations, information storage mechanism 1110 might include other similar instrumentalities for allowing computer programs or other instructions or data to be loaded into computing system 1100. Such instrumentalities might include, for example, a fixed or removable storage unit 1122 and an interface 1120. Examples of such storage units 1122 and interfaces 1120 can include a program cartridge and cartridge interface, a removable memory (for example, a flash memory or other removable memory module) and memory slot, a flash drive and associated slot (for example, a USB drive), a PCMCIA slot and card, and other fixed or removable storage units 1122 and interfaces 1120 that allow software and data to be transferred from the storage unit 1122 to computing system 1100.

Computing system 1100 might also include a communications interface 1124. Communications interface 1124 might be used to allow software and data to be transferred between computing system 1100 and external devices. Examples of communications interface 1124 might include a modem or softmodem, a network interface (such as an Ethernet, network interface card, WiMedia, IEEE 802.XX, Bluetooth® or other interface), a communications port (such as for example, a USB port, IR port, RS232 port, or other port), or other communications interface. Software and data transferred via communications interface 1124 might typically be carried on signals, which can be electronic, electromagnetic (which includes optical) or other signals capable of being exchanged by a given communications interface 1124. These signals might be provided to communications interface 1124 via a channel 1128. This channel 1128 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 1108, storage unit 1120, media 1114, and channel 1128. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing system 1100 to perform features or functions of the disclosed technology as discussed herein.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

While various examples of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent module names other than those depicted herein can be applied to the various partitions. Additionally, with regard to flow diagrams, operational descriptions and method claims, the order in which the steps are presented herein shall not mandate that various examples be implemented to perform the recited functionality in the same order unless the context dictates otherwise.

Although the disclosed technology is described above in terms of various example examples and implementations, it should be understood that the various features, aspects and functionality described in one or more of the individual examples are not limited in their applicability to the particular example with which they are described, but instead can be applied, alone or in various combinations, to one or more of the other examples of the disclosed technology, whether or not such examples are described and whether or not such features are presented as being a part of a described example. Thus, the breadth and scope of the technology disclosed herein should not be limited by any of the above-described example examples. It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide example instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. The term comprising is intended herein to be open-ended, including not only the recited elements, but any additional elements as well. Likewise, where this document refers to technologies that would be apparent or known to one of ordinary skill in the art, such technologies encompass those apparent or known to the skilled artisan now or at any time in the future. To the extent applicable, the terms "first," "second," "third," etc. herein are merely employed to show the respective objects described by these terms as separate entities and are not meant to connote a sense of chronological order, unless stated explicitly otherwise herein.

The term "coupled" refers to direct or indirect joining, connecting, fastening, contacting or linking, and may refer to various forms of coupling such as physical, optical, electrical, fluidic, mechanical, chemical, magnetic, electromagnetic, communicative or other coupling, or a combination of the foregoing. Where one form of coupling is specified, this does not imply that other forms of coupling are excluded. For example, one component physically coupled to another component may reference physical attachment of or contact between the two components (directly or indirectly), but does not exclude other forms of coupling between the components such as, for example, a communications link (e.g., an RF or optical link) also communicatively coupling the two components. Likewise, the various terms themselves are not intended to be mutually exclusive. For example, a fluidic coupling, magnetic coupling or a mechanical coupling, among others, may be a form of physical coupling.

The presence of broadening words and phrases such as "one or more," "at least," "but not limited to" or other like phrases in some instances shall not be read to mean that the narrower case is intended or required in instances where such broadening phrases may be absent. The use of the term "component" does not imply that the elements or functionality described or claimed as part of the component are all configured in a common package. Indeed, any or all of the various elements of a component, including structural elements, can be combined in a single package or separately maintained and can further be distributed in multiple groupings or packages.

Additionally, the various examples set forth herein are described in terms of example diagrams and other illustrations. As will become apparent to one of ordinary skill in the art after reading this document, the illustrated examples and their various alternatives can be implemented without confinement to the illustrated examples. For example, block diagrams and their accompanying description should not be construed as mandating a particular architecture or configuration.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

We claim:

1. An imaging system, comprising;
   a sample stage comprising a surface to support a sample to be scanned by the imaging system;

an optical stage having an objective lens, the optical stage being positionable relative to the sample stage;

an actuator physically coupled to at least one of the sample stage and the optical stage to move the sample stage relative to the optical stage;

a servo circuit to control the actuator;

a first set of control parameters to control the servo circuit;

a second set of control parameters to control the servo circuit; and a servo control circuit to apply the first set of control parameters to the servo circuit when the imaging system is operating in a first mode of operation and to apply the second set of control parameters to the servo circuit when the imaging system is operating in a second mode of operation, wherein the servo control circuit comprises a mode detection circuit to detect the mode of operation of the imaging system and a parameter selection circuit to apply the first set of control parameters or the second set of control parameters corresponding to the detected first mode of operation or second mode of operation.

2. The imaging system of claim 1, wherein the imaging system is a sequencer and the first mode of operation is a focus model generation mode, and the second mode of operation is a sequencing mode.

3. The imaging system of claim 1, wherein the servo control circuit further detects the mode of operation of the imaging system and selects the set of control parameters to apply for the detected mode of operation.

4. The imaging system of claim 3, wherein the servo control circuit applies the first or second set of control parameters that are identified as being the set of control parameters for the detected mode of operation.

5. The imaging system of claim 3, wherein at least one of the first and second sets of control parameters is optimized to account for structural characteristics of the imaging system.

6. The imaging system of claim 5, wherein optimizing at least one of the first and second sets of control parameters comprises operating the imaging system, scanning through a range of values of a control parameter of a set of the first and second sets of control parameters, measuring stability of the servo circuit during the scanning and selecting a value of the control parameter.

7. The imaging system of claim 5, wherein optimizing at least one of the first and second sets of control parameters comprises operating the imaging system, scanning through a range of values of a plurality of control parameters of a set of the first and second sets of control parameters, measuring stability of the servo circuit during the scanning and identifying optimal settings for the plurality of control parameters.

8. The imaging system of claim 1, wherein the imaging system further comprises focus tracking circuitry electrically coupled to the optical stage; and wherein the servo control circuit is further to enable feedback from the focus tracking circuitry to the servo circuit when the imaging system is operating in a scanning mode of operation and to disable feedback from the focus tracking circuitry to the servo circuit when the imaging system is operating in focus model generation mode of operation.

9. The imaging system of claim 1, wherein the control parameters include servo loop gains and filter values.

10. The imaging system of claim 1, wherein the actuator is physically coupled to the sample stage to move the sample stage to adjust a distance between the sample stage and the optical stage.

11. The imaging system of claim 1, further comprising a plurality of actuators physically coupled to the sample stage to adjust a tilt of the sample stage.

12. The imaging system of claim 1, wherein the actuator is physically coupled to the optical stage to move the optical stage to adjust a distance between the sample stage and the optical stage.

13. The imaging system of claim 12, wherein the actuator comprises at least one of a piezoelectric device, a voice coil, and a drive motor.

14. The imaging system of claim 1, wherein the sample is contained in a flow cell or on a slide.

15. In an imaging system, a method of servo control, comprising:

during operation of the imaging system, a mode detection circuit determining that the imaging system is operating in a first mode of operation;

a servo control circuit determining a first set of control parameters selected for the first mode of operation;

the servo control circuit applying the determined first set of control parameters to a servo circuit of the imaging system, wherein the servo circuit controls operation of an actuator physically coupled to at least one of a sample stage and an optical stage of the imaging system to move the sample stage relative to the optical stage; and upon the mode detection circuit determining during operation of the imaging system that the imaging system has switched to operating in a second mode of operation, the servo control circuit determining a second set of control parameters selected for the second mode of operation and applying the determined second set of control parameters to a servo circuit.

16. The method of claim 15, wherein the servo control circuit comprises a mode detection circuit detecting the mode of operation of the imaging system and a parameter selection circuit applying the set of control parameters corresponding to the detected mode of operation.

17. The method of claim 15, further comprising the servo control circuit detecting the mode of operation of the imaging system and selecting the set of control parameters to apply for the detected mode of operation.

18. The method of claim 17, further comprising the servo control circuit applying the first or second set of control parameters that are identified as being the set of control parameters for the detected mode of operation.

19. The method of claim 15, further comprising optimizing at least one of the first and second sets of control parameters to account for structural characteristics of the imaging system.

20. The method of claim 19, wherein optimizing at least one of the first and second sets of control parameters comprises operating the imaging system, scanning through a range of values of a control parameter of a set of the first and second sets of control parameters, measuring stability of the servo circuit during the scanning and selecting a value of the control parameter.

21. The method of claim 19, wherein optimizing at least one of the first and second sets of control parameters comprises operating the imaging system, scanning through a range of values of a plurality of control parameters of a set of the first and second sets of control parameters, measuring stability of the servo circuit during the scanning and identifying optimal settings for the plurality of control parameters.

22. The method of claim 15, wherein the servo control circuit further enables feedback from focus tracking circuitry to the servo circuit when the imaging system is operating in a scanning mode of operation and to disable feedback from the focus tracking circuitry to the servo circuit when the imaging system is operating in focus model generation mode of operation.

23. The method of claim 15, wherein the control parameters include servo loop gains and filter values.

24. The method of claim 15, further comprising the actuator moving the sample stage to adjust a distance between the sample stage and the optical stage.

25. The method of claim 24, wherein the actuator comprises at least one of a piezoelectric device, a voice coil, and a drive motor.

26. The method of claim 15, wherein the imaging system is a sequencer and the first mode of operation is a focus model generation mode, and the second mode of operation is a sequencing mode.

27. An imaging system, comprising:
a sample stage comprising a surface to support a sample to be scanned by the imaging system;
an optical stage having an objective lens, the optical stage being positionable relative to the sample stage;
focus tracking circuitry coupled to the optical stage;
an actuator physically coupled to at least one of the sample stage and the optical stage to move the sample stage relative to the optical stage based on information from the focus tracking circuitry;
a servo circuit to control the actuator; and
a servo control circuit to enable feedback from the focus tracking circuitry to the servo circuit when the imaging system is operating in a scanning mode of operation and to disable feedback from the focus tracking circuitry to the servo circuit when the imaging system is operating in focus model generation mode of operation.

28. In an imaging system, a method of servo control, comprising:
during operation of the imaging system, a mode detection circuit determining whether the imaging system is operating in a scanning mode of operation or a focus model generation mode of operation;
a servo circuit controlling movement of an optical stage relative to a sample stage in the imaging system; and
a servo control circuit enabling feedback from focus tracking circuitry to the servo circuit when the imaging system is operating in a scanning mode of operation and disabling feedback from the focus tracking circuitry to the servo circuit when the imaging system is operating in focus model generation mode of operation.

29. An imaging system, comprising:
a sample stage comprising a surface to support a sample to be scanned by the imaging system;
an optical stage having an objective lens, the optical stage being positionable relative to the sample stage;
an actuator physically coupled to at least one of the sample stage and the optical stage to move the sample stage relative to the optical stage;
a servo circuit to control the actuator;
a first set of control parameters to control the servo circuit;
a second set of control parameters to control the servo circuit;
a servo control circuit to apply the first set of control parameters to the servo circuit when the imaging system is operating in a first mode of operation and to apply the second set of control parameters to the servo circuit when the imaging system is operating in a second mode of operation; and
focus tracking circuitry electrically coupled to the optical stage;
wherein the servo control circuit is further to enable feedback from the focus tracking circuitry to the servo circuit when the imaging system is operating in a scanning mode of operation and to disable feedback from the focus tracking circuitry to the servo circuit when the imaging system is operating in focus model generation mode of operation.

30. An imaging system, comprising:
a sample stage comprising a surface to support a sample to be scanned by the imaging system;
an optical stage having an objective lens, the optical stage being positionable relative to the sample stage;
an actuator physically coupled to at least one of the sample stage and the optical stage to move the sample stage relative to the optical stage;
a servo circuit to control the actuator;
a first set of control parameters to control the servo circuit;
a second set of control parameters to control the servo circuit; and
a servo control circuit to apply the first set of control parameters to the servo circuit when the imaging system is operating in a first mode of operation, to apply the second set of control parameters to the servo circuit when the imaging system is operating in a second mode of operation, to detect the first mode of operation or the second mode of operation of the imaging system, to select the first set of control parameters or the second set of control parameters to apply for the detected first mode of operation or second mode of operation, and to apply the first set of control parameters or the second set of control parameters that are identified as being the set of control parameters for the detected first mode of operation or the second mode of operation.

31. An imaging system, comprising:
a sample stage comprising a surface to support a sample to be scanned by the imaging system;
an optical stage having an objective lens, the optical stage being positionable relative to the sample stage;
an actuator physically coupled to at least one of the sample stage and the optical stage to move the sample stage relative to the optical stage;
a servo circuit to control the actuator;
a first set of control parameters to control the servo circuit;
a second set of control parameters to control the servo circuit; and
a servo control circuit to apply the first set of control parameters to the servo circuit when the imaging system is operating in a first mode of operation, to apply the second set of control parameters to the servo circuit when the imaging system is operating in a second mode of operation, to detect the first mode of operation or the second mode of operation of the imaging system, and to select the first set of control parameters or the second set of control parameters to apply for the detected first mode of operation or the second mode of operation,
wherein at least one of the first and second sets of control parameters is optimized to account for structural characteristics of the imaging system.

32. The imaging system of claim 31, wherein optimizing at least one of the first and second sets of control parameters comprises operating the imaging system, scanning through a range of values of a control parameter of a set of the first and second sets of control parameters, measuring stability of the servo circuit during the scanning and selecting a value of the control parameter.

33. The imaging system of claim 31, wherein optimizing at least one of the first and second sets of control parameters comprises operating the imaging system, scanning through a range of values of a plurality of control parameters of a set of the first and second sets of control parameters, measuring stability of the servo circuit during the scanning and identifying optimal settings for the plurality of control parameters.

\* \* \* \* \*